(12) United States Patent
Watrous

(10) Patent No.: US 6,544,189 B2
(45) Date of Patent: Apr. 8, 2003

(54) HANDHELD SENSOR FOR ACOUSTIC DATA ACQUISITION

(75) Inventor: Raymond Watrous, Belle Mead, NJ (US)

(73) Assignee: Zargis Medical Corp., Princeton, NJ (US)

( * ) Notice: Subject to any disclaimer, the term of this patent is extended or adjusted under 35 U.S.C. 154(b) by 0 days.

(21) Appl. No.: 09/893,118

(22) Filed: Jun. 27, 2001

(65) Prior Publication Data

US 2002/0038089 A1 Mar. 28, 2002

Related U.S. Application Data

(63) Continuation-in-part of application No. 09/670,053, filed on Sep. 25, 2000.

(51) Int. Cl.$^7$ .................................................. A61B 5/04
(52) U.S. Cl. ........................................ 600/528; 128/903
(58) Field of Search ................................ 600/437, 438, 600/586, 587, 528, 382–394

(56) References Cited

U.S. PATENT DOCUMENTS

| | | | | |
|---|---|---|---|---|
| 4,218,584 A | * | 8/1980 | Attenburrow | 119/29 |
| 4,362,164 A | * | 12/1982 | Little et al. | 600/528 |
| 4,458,687 A | * | 7/1984 | Dickson | 600/528 |
| 5,862,803 A | * | 1/1999 | Besson et al. | 128/903 |
| 6,409,684 B1 | * | 6/2002 | Wilk | 600/586 |

* cited by examiner

Primary Examiner—Francis J. Jaworski
(74) Attorney, Agent, or Firm—Donald B. Paschburg

(57) ABSTRACT

According to an embodiment of the present invention, an acoustic signal sensing apparatus is provided. The apparatus includes a housing having an apertured posterior and three studs wherein at least one stud is an electrode providing a temporal reference signal and a sensing unit contacting a patient and capturing an acoustic cardiovascular signal and the temporal reference signal, wherein a portion of the sensing unit is located within the housing. The apparatus further includes a telemetry sensor connected to the sensing unit, communicating the acoustic signal, the temporal reference signal, and a position of the sensing unit with respect to the patient to a data processor.

22 Claims, 4 Drawing Sheets

HANDHELD SENSOR FOR ACOUSTIC DATA ACQUISITION

This a continuation-in-part of the copending non-provisional application Ser. No. 09/670,053, filed Sep. 25, 2000.

BACKGROUND OF THE INVENTION

1. Field of the Invention

The present invention is directed to a hand held sensor for acoustic data acquisition in medical diagnosis, and more particularly, a sensor having a cursor control for a position-indicating display.

2. Description of Related Art

Stethoscopes are relied upon for acoustic diagnosis in medicine, in particular, for the diagnosis of cardiovascular disease. However, stethoscopes have limited functionality, both in design and implementation. The stethoscope itself transfers only a small fraction of the acoustic signal at the chest surface to the listener's ears, and filters the cardiac acoustic signal in the process.

In particular, with respect to auscultation of the heart, much of the signal energy in many heart sounds is below the threshold of human hearing. This situation is compounded by the degradation of the listener's hearing which can be associated with, for example, age and/or exposure to excessive noise. Auscultation also relies on correctly determining which of the primary heart sounds correspond with the systolic and diastolic phase of the heart, which is made more difficult when the systolic and diastolic intervals are more equal, typically at elevated heart rates. Auscultation also relies on detecting the correct sequence of brief events occurring close in time, something that is difficult for human listeners.

Learning auscultation is also difficult because diagnostic instructional manuals rely on subjective descriptions of heart sounds, which need practice to appreciate. Furthermore, the practice and teaching of the clinical skill of auscultation of the heart has declined among physicians, this is partly due to non-reimbursement policies of providers or insurers. Recent tests have demonstrated that physicians can identify, reliably, only a small number of standard heart sounds and murmurs. Consequently, serious heart murmurs in many patients go undetected by physicians.

In addition, the decline in auscultation skills has led to an over-reliance on echocardiography, resulting in a large number of unnecessary and expensive diagnostic studies.

Therefore, a need exists for an acoustic data acquisition device for use in medical diagnosis.

SUMMARY OF THE INVENTION

According to an embodiment of the present invention, an acoustic signal sensing apparatus is provided. The acoustic signal sensing apparatus includes a housing having an apertured posterior and a plurality of studs, an acoustic sensing unit, wherein a portion of the sensing unit is located within the housing, and a telemetry sensor connected to the sensing unit and a data processor.

At least one stud is an electrode providing a temporal reference signal detectable by the acoustic sensing unit. The studs contact the patient and support the housing. The studs substantially resist involuntary lateral movement of the housing. The plurality of studs is at least three. The studs can extend from the posterior. The studs can extend through the posterior. The studs can be connected to the posterior.

The acoustic sensing unit senses a cardiovascular signal.

According to an embodiment of the present invention, an apparatus for sensing an acoustic signal is provided including a housing means having an apertured posterior and a plurality of studs. The apparatus includes a sensing unit means for interfacing a patient by contact with the patient and capturing the acoustic signal, wherein a portion of the sensing unit means is located within the housing. The apparatus further includes a telemetry sensor means connected to the sensing unit means for communicating the acoustic signal and a position of the sensing unit means with respect to the patient to a data processor means.

At least one stud is an electrode providing a temporal reference signal detectable by the sensing unit means. The studs contact the patient and support the housing means. The studs substantially resist involuntary lateral movement of the housing means. The plurality of studs is at least three. Each stud can extend from the posterior, through the posterior, or be connected to the posterior.

The sensing unit means senses a cardiovascular signal.

According to an embodiment of the present invention, an acoustic signal sensing apparatus is provided. The apparatus includes a housing having an apertured posterior and three studs wherein at least one stud is an electrode providing a temporal reference signal and a sensing unit contacting a patient and capturing an acoustic cardiovascular signal and the temporal reference signal, wherein a portion of the sensing unit is located within the housing. The apparatus further includes a telemetry sensor connected to the sensing unit, communicating the acoustic signal, the temporal reference signal, and a position of the sensing unit with respect to the patient to a data processor.

BRIEF DESCRIPTION OF THE DRAWINGS

Preferred embodiments of the present invention will be described below in more detail, with reference to the accompanying drawings.

It should be noted that throughout the drawings, like numbers indicate like elements.

DETAILED DESCRIPTION OF PREFERRED EMBODIMENTS

Figure 1A:
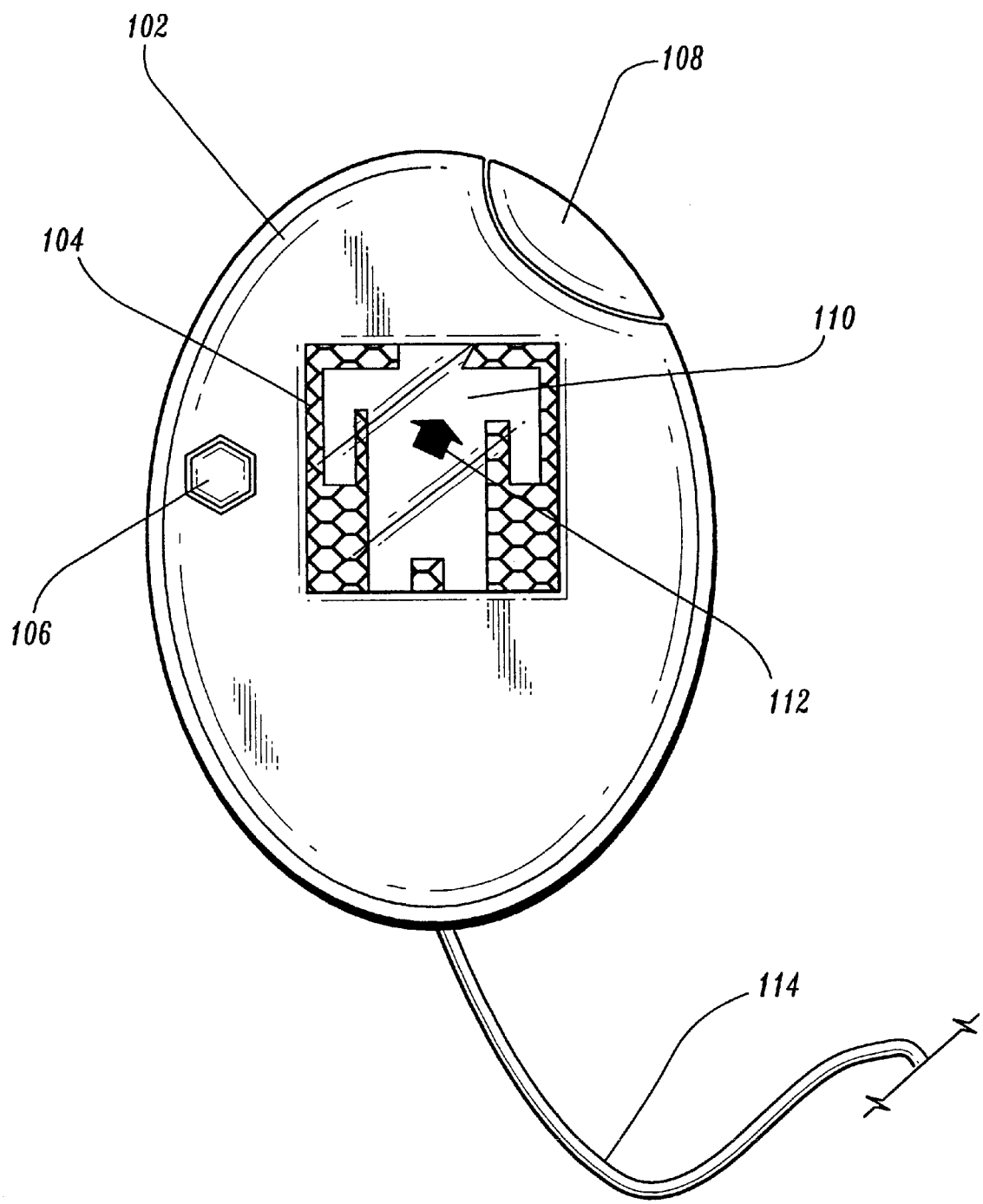
FIG. 1A is a top-down view of an acoustic sensing device according to one embodiment of the present invention.
Figure 1B:
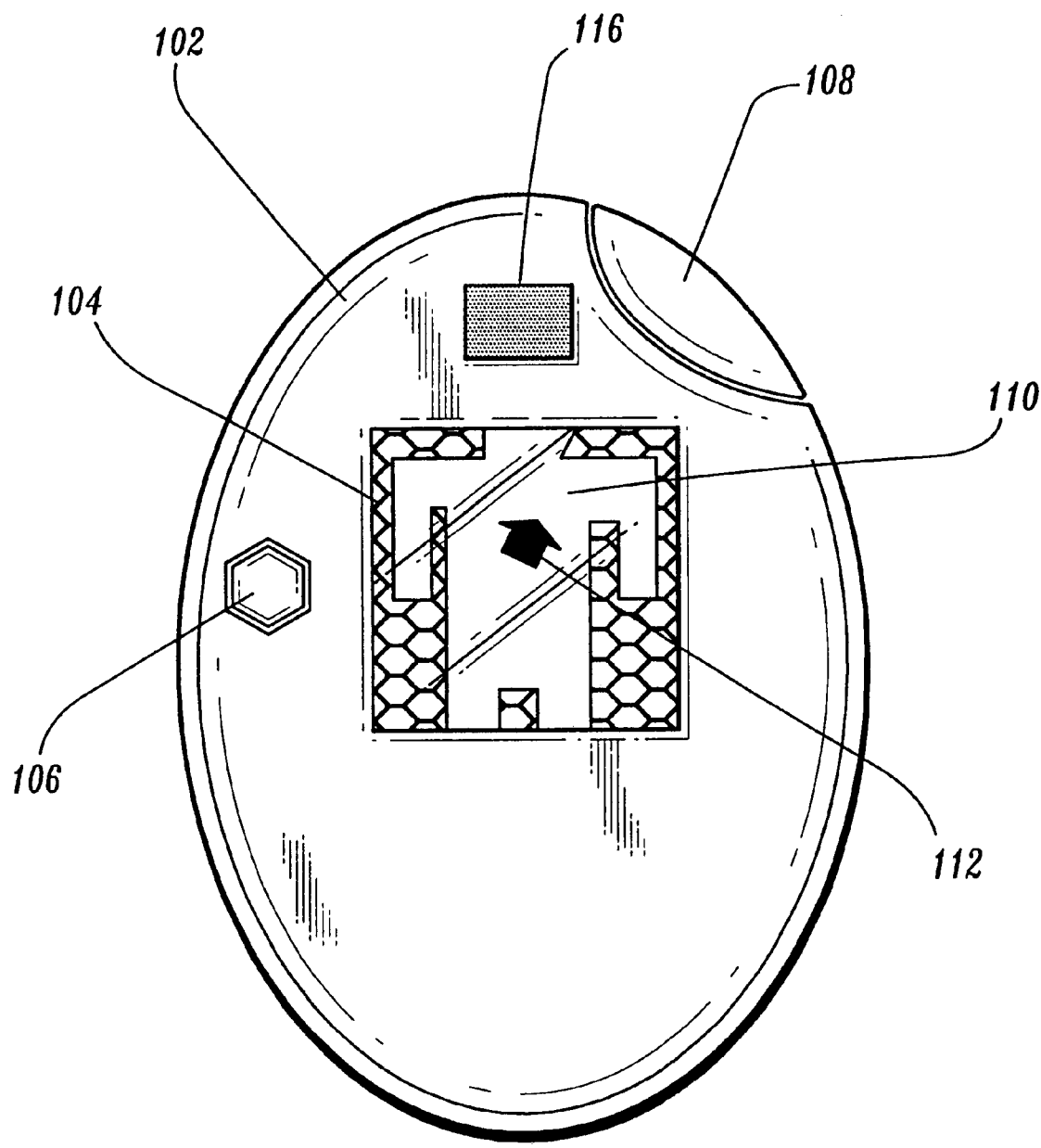
FIG. 1B is a top-down view of an acoustic sensing device having an infrared port according to another embodiment of the present invention.

Referring to FIG. 1, a hand-held device, or "pod" 102, according to one embodiment of the present invention, incorporates an acoustic sensing element 206 (shown in FIG. 2) for capturing sound waves, and a position-indicating display 104 for displaying telemetry data.

The acoustic sensing element 206 extends partially from an aperture on the bottom of the pod. The sensing element is spring-mounted 204 in order to apply moderate and controlled pressure against the chest or back of a patient. The spring mounting gives the sensing element a measure of mechanical independence from the sensor pod to reduce motion artifacts. Alternatively, mounting apparatus such as rubber mounts, leaf-springs, coil springs, a pivot joint, fluids, jells, etc., can be used alone or in combination to support the sensing element. In another embodiment of the present invention, the sensor is in a static position, flush with the bottom of the pod, where the pod and sensor form a continuous surface. Further, an acoustically conductive lubricating agent may be applied to the skin of the patient to facilitate acoustic interfacing between the sensor and the patient.

Figure 2:
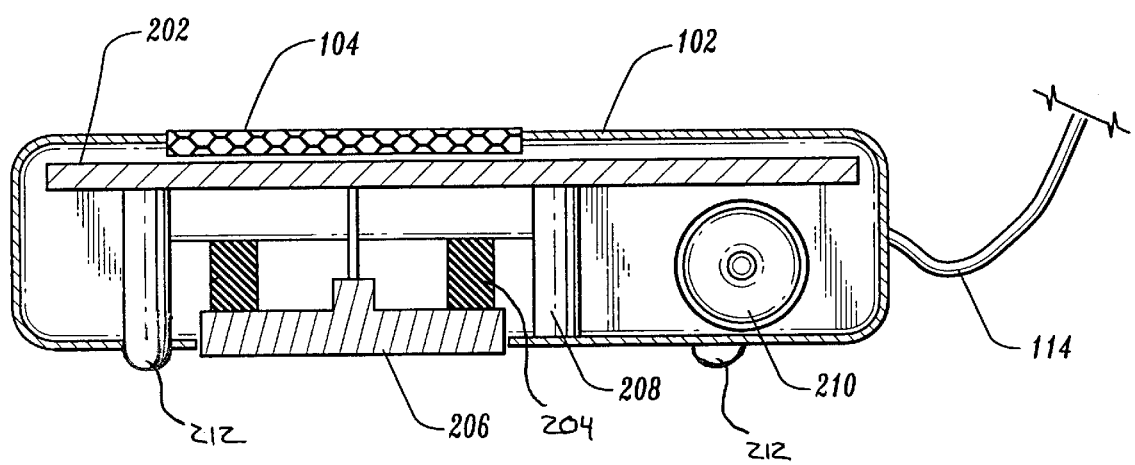
FIG. 2 is an exposed side view of an acoustic sensing device according to yet another embodiment of the present invention.
Figure 3:
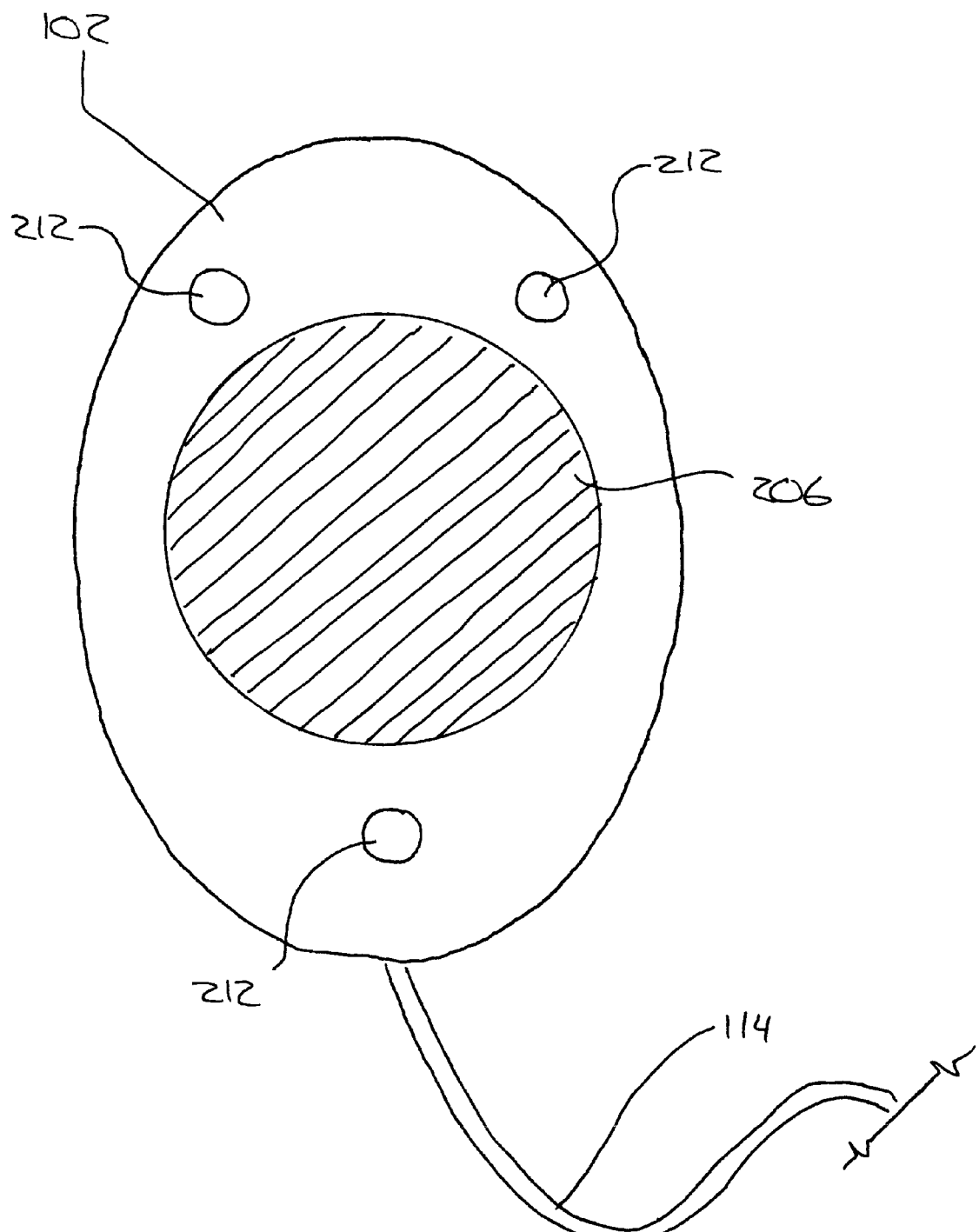
FIG. 3 is a bottom-up view of an acoustic sensing device according to one embodiment of the present invention.

Referring to FIGS. 2 and 3, the pod 102 can further comprise supporting studs 212. These studs 212 protrude from the bottom, or posterior, of the pod 102, and are preferably rounded and smooth. An individual stud may be attached to the posterior of the pod 102, pass through the posterior, or be an extension of the pod 102. Different studs may be used in combination on the pod 102.

The studs 212 provide direct contact with the patient. The studs 212 stabilize the sensor pod 102 in a fixed position (laterally) with respect to the patient. Any number of studs 212 may be used. In a preferred embodiment, three studs are provided. The studs 212 stabilize the position of the pod with respect to the contours and planes of the patient. The mounting apparatus brings the sensor into contact with the patient. In one embodiment of the present invention, one or more studs 212 are formed of a conductive material, such as brass, and can be implemented as dry electrocardiogram (ECG/EKG) electrodes. These electrodes can provide a temporal reference or base-line signal (pressure) for interpretation and analysis of the cardiac acoustic signal (pressure).

The pod 102 houses a printed-circuit board 202, supported by studs 208. Electronics mounted on the printed-circuit board include preamplifier circuitry, cursor control circuitry, telemetry circuitry, and/or other circuitry for processing signals to and from the sensor 206. In another embodiment of the present invention, the electronics include the preamplifier circuitry and cursor control circuitry. Alternatively, the electronics or another control board can be located external to the pod 102, connected to the sensor via a cable 114.

The pod 102 also houses a battery 210 for providing power to the electronics. The power can also be provided via the cable 114 connecting the pod 102 to a diagnostic support or data processing system.

A planar liquid crystal display (LCD) 104 is mounted on the surface of the pod 102. A rocker switch 106, preferably with two axes of motion, is flush-mounted on the left side of the pod 102, and a contoured switch 108 is embedded in the upper right surface of the pod 102. The rocker switch 106 controls the position of a visible cursor 112 that registers the sensor position on an outline of the thorax 110, which is overlaid on the LCD 104. Movement of the rocker switch 106 is translated into movement of the cursor on the LCD 104 by the cursor control circuitry. The contoured switch 108 may be used to signal that the sensor is in the desired position and that the sensor position is correctly registered on the LCD 104.

Through the use of the LCD 104, rocker switch 106, and contoured switch 108, the data acquisition and processing system can acquire positional information. The positional information preferably includes the position of the sensor relative to the patient and/or elements of the patient's cardiovascular system. One with ordinary skill in the art would recognize, in light of the present invention, that other control mechanisms are possible, for example, a joystick, touch-pad, trackball, or scrolling wheel.

The acoustic signal is pre-amplified by the pre-amplifying circuitry, while the positional information is processed by the telemetry circuitry. The amplified acoustic signal and processed positional information can then be transmitted to the data processing system either by a cable, or remotely using wireless technology. The telemetry circuitry preferably transmits the acoustic signal and positional data. A wireless connection using, for example, wireless application protocol (WAP) or infrared (IR), may be made using a data transmission device, such as an antenna or IR port 116. Other transmission protocols are contemplated by the present invention.

Having described embodiments for a handheld sensor for acoustic data acquisition, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

What is claimed is:

1. An acoustic signal sensing apparatus comprising:
   a housing having an apertured posterior surface and a plurality of studs coupled to the apertured posterior surface for interfacing with a patient;
   an acoustic sensing unit, wherein a portion of the sensing unit is located within the housing; and
   a telemetry sensor connected to the sensing unit and a data processor, wherein the telemetry sensor receives manually determined positional information.

2. The apparatus of claim 1, wherein at least one stud is an electrode providing a temporal reference signal detectable by the acoustic sensing unit.

3. The apparatus of claim 1, wherein the studs contact the patient and support the housing.

4. The apparatus of claim 1, wherein the studs substantially resist involuntary lateral movement of the housing.

5. The apparatus of claim 1, wherein the plurality of studs is at least three.

6. The apparatus of claim 1, wherein the studs extend from the posterior.

7. The apparatus of claim 1, wherein the studs extend through the posterior.

8. The apparatus of claim 1, wherein the studs are connected to the posterior.

9. The apparatus of claim 1, wherein the acoustic sensing unit senses a cardiovascular signal.

10. The acoustic signal sensing apparatus of claim 1, wherein sensing unit interfaces with the patient and receives acoustic signals.

11. The acoustic signal sensing apparatus of claim 1, further comprising:
    a display located anteriorally on the housing;
    a control means for positioning a cursor in the display, indicating a position of the sensing unit with respect to the patient.

12. An apparatus for sensing an acoustic signal comprising:
    a housing having an apertured posterior surface and a plurality of studs coupled to the apertured posterior surface for interfacing with a patient;
    sensing unit means for interfacing the patient by contact with the patient and capturing the acoustic signal, wherein a portion of the sensing unit means is located within the housing; and telemetry sensor means connected to the sensing unit means for communicating the acoustic signal and a position of the sensing unit means with respect to the patient to a data processor means, wherein the telemetry sensor receives manually determined positional information.

13. The apparatus of claim 12, wherein at least one stud is an electrode providing a temporal reference signal detectable by the sensing unit means.

14. The apparatus of claim 12, wherein the studs contact the patient and support the housing means.

15. The apparatus of claim 12, wherein the studs substantially resist involuntary lateral movement of the housing means.

16. The apparatus of claim 12, wherein the plurality of studs is at least three.

17. The apparatus of claim 12, wherein the studs extend from the posterior.

18. The apparatus of claim 12, wherein the studs extend through the posterior.

19. The apparatus of claim 12, wherein the studs are connected to the posterior.

20. The apparatus of claim 12, wherein the sensing unit means senses a cardiovascular signal.

21. The acoustic signal sensing apparatus of claim 12, further comprising:

a display located anteriorally on the housing;

a control means for positioning a cursor in the display, indicating a position of the sensing unit with respect to the patient; and a switch for indicating that the manually determined positional information has a desired registration.

22. An acoustic signal sensing apparatus comprising:

a housing having an apertured posterior surface and three studs coupled to the apertured posterior surface for interfacing with a patient, wherein at least one stud is an electrode providing a temporal reference signal;

a sensing unit contacting the patient and capturing an acoustic cardiovascular signal and the temporal reference signal, wherein a portion of the sensing unit is located within the housing;

a telemetry sensor connected to the sensing unit, communicating the acoustic signal, the temporal reference signal, and a position of the sensing unit with respect to the patient to a data processor, wherein the telemetry sensor receives manually determined positional information;

a display located anteriorally on the housing; and a control means for positioning a cursor in the display, indicating a position of the sensing unit with respect to the patient.

* * * * *